United States Patent [19]

Smith, Jr.

[11] 3,975,453

[45] Aug. 17, 1976

[54] PROCESS FOR PREPARING BUTYNYLLITHIUM

[75] Inventor: William Novis Smith, Jr., Stamford, Conn.

[73] Assignee: Foote Mineral Company, Exton, Pa.

[22] Filed: Feb. 24, 1975

[21] Appl. No.: 552,317

[52] U.S. Cl. ............................................. 260/665 R
[51] Int. Cl.² ........................................... C07F 1/02
[58] Field of Search ................................. 260/665 R

[56] References Cited
UNITED STATES PATENTS

| | | | |
|---|---|---|---|
| 2,605,295 | 7/1952 | Garner et al. | 260/665 R |
| 3,410,918 | 11/1968 | Beumel et al. | 260/665 R |
| 3,418,385 | 12/1968 | Skinner et al. | 260/665 R |
| 3,441,621 | 4/1969 | Tedeschi et al. | 260/665 R |
| 3,660,536 | 5/1972 | Ayano et al. | 260/665 R |

OTHER PUBLICATIONS

Chemical Abstracts, vol. 28, 5430–5431 (1934).

*Primary Examiner*—Helen M. S. Sneed
*Attorney, Agent, or Firm*—Howson & Howson

[57] ABSTRACT

Butynyllithium is prepared by passing a gaseous unsaturated hydrocarbon selected from the group consisting of 1,2-butadiene or a mixture of 1,2-butadiene, 1,3-butadiene, 1-butyne and 2-butyne into a slurry of lithium metal dispersed in a strong coordinating ether solvent, said slurry being under a substantially oxygen-free atmosphere.

8 Claims, No Drawings

PROCESS FOR PREPARING BUTYNYLLITHIUM

DESCRIPTION OF THE INVENTION

This invention relates to a process for preparing butynyllithium, and it is the object of this invention to provide a new method for preparing butynyllithium which is economical since it utilizes relatively inexpensive starting materials and produces a high yield of the desired product.

U.S. Pat. No. 3,410,918 describes a process for preparing propynylsodium and propynyllithium in which a gaseous mixture of propyne and allene in which the weight ratio of propyne to allene is from about 1:1 to about 4:1 is contacted with a slurry of sodium metal or lithium metal containing a small amount of sodium in an inert, ether type solvent or certain aromatic and aliphatic hydrocarbon solvents.

According to the present invention, butynyllithium, having the empirical formula $CH_3CH_2C \equiv CLi$ is prepared in a process which comprises passing a gaseous unsaturated hydrocarbon selected from the group consisting of 1,2-butadiene or a mixture of 1,2-butadiene, 1,3-butadiene, 1-butyne and 2-butyne, into a slurry of finely-divided lithium metal dispersed in a strong coordinating ether solvent, said slurry being under a substantially oxygen-free atmosphere.

The lithium reactant employed will advantageously be finely-divided; that is, the lithium reactant will have a particle size of −30 mesh, and preferably −100 mesh. Lithium metal may be utilized in the well known dispersion form. Such dispersions are prepared by rapidly stirring molten lithium metal into an inert liquid, such as mineral oil or toluene, so that the metal solidifies as very tiny droplets, generally no more than about 100 microns in size and most usually from about 25 to about 75 microns in size. The finely-divided lithium metal may be filtered from the liquid to provide, after washing and drying, what is known as a dry dispersion or powder.

In the practice of the present invention, it is preferred that pure lithium metal be utilized; that is, the lithium metal should have little, if any, sodium associated with it. In this regard, if lithium metal containing as much as 1%, by weight, sodium is utilized as the lithium reactant the yield of butynyllithium produced will be decreased due to increased polymerization of the 1,3-butadiene component in the gaseous mixture during the reaction. This is borne out by the fact that it has not been possible to produce butynylsodium by a process analogous to the present method wherein sodium metal is substituted for lithium metal, again for the reason that the 1,3-butadiene component of the gaseous mixture is thought to undergo rapid polymerization in the presence of sodium metal. Of course, if 1,2-butadiene alone or a mixture of 1,2-butadiene, 1,3-butadiene, 1-butyne and 2-butyne in which the 1,3-butadiene content is relatively low (e.g. less than 8%, by weight) is utilized to prepare the butynyllithium the sodium content of the lithium metal becomes less critical and lithium metal containing up to 1%, by weight, sodium may be utilized in the process.

The gaseous unsaturated hydrocarbon utilized in forming butynyllithium may be substantially pure 1,2-butadiene (e.g. 99% 1,2-butadiene) or a mixture of 1,2-butadiene, 1,3-butadiene 1-butyne and 2-butyne produced as an inexpensive by-product in the manufacture of butadiene. The by-product mixture may also contain other hydrocarbons which are inert under the reaction conditions of the present process; however, to be useful in the present process the gaseous mixture should not contain more than 60%, by weight, 1,3-butadiene and while the proportion of 1,2-butadiene, 1-butyne and 2-butyne in the gaseous mixture is not critical, the mixture should contain from about 5% to about 100%, preferably from about 15% to about 100%, by weight, based on the weight of the mixture, of 1,2-butadiene, 1,3-butadiene, 1-butyne and 2-butyne components. The gaseous material should be free of air and moisture or acidic gases which would interfere with the reaction. Such gaseous mixtures are available commercially and are produced, for example, as by-products in 1,3-butadiene or other $C_4$ fractions in hydrocarbon cracking processes.

Because 1,3-butadiene is known to polymerize when combined with lithium metal in tetrahydrofuran, those skilled in the art reasonably would expect that 1,2-butadiene and 1,3-butadiene would be polymerized in any reaction between 1,2-butadiene and 1,3-butadiene and lithium metal in an inert solvent, resulting in gellation or solidification of the reaction mixture and precluding the formation of butynyllithium. Contrary to this expectation, the surprising finding has been made that gaseous mixtures of 1,2-butadiene, 1-butyne and 2-butyne, including mixtures of these gases with 1,3-butadiene which do not contain more than 60%, by weight, of 1,3-butadiene, can be converted into butynyllithium when reacted with lithium metal in a strong coordinating ether solvent. While the precise reason for this phenomenon is not understood, it is thought likely that the acetylenic components of the gaseous mixture, e.g. 1-butyne and 2-butyne, greatly hinder and reduce the polymerization of 1,2-butadiene and any 1,3-butadiene present, limiting polymerization of such components to the formation of liquid dimers, trimers and tetramers, thereby permitting formulation of the desired butynyllithium.

The process of the present invention is carried out in a solvent consisting essentially of a strong coordinating ether solvent. Suitable strong coordinating ether solvents include tetrahydrofuran, tetrahydropyran, dioxane, ethylene glycol dimethyl ether, commonly known as "glyme", ethylene glycol diethyl ether, and other "glyme" analogs, such as the dimethyl and diethyl ethers of diethylene, triethylene and tetraethylene glycols, and mixtures of two or more of these solvents. Tetrahydrofuran is the preferred solvent. The amount of solvent utilized in the reaction is not critical since it merely serves as a liquid medium for holding the lithium metal in a dispersed condition while the gaseous 1,2-butadiene or mixture of 1,2-butadiene, 1,3-butadiene, 1-butyne and 2-butyne is passed therethrough. Generally, sufficient lithium metal will be dispersed in the solvent to provide a molar concentration of lithium in the solvent of from about 0.5 to about 4. Attempts to practice the present invention utilizing solvents such as xylene, benzene and diethyl ether as dispersing agents for the lithium metal have been found to be unsuccessful.

The principal reaction which occurs in the present process is that between lithium metal and 1,2-butadiene and any 1-butyne component of the gaseous mixture in a mol ratio of about 2:3. Hydrogen is produced as a by-product of this reaction; the hydrogen produced causes reduction of a portion of the dienes and acetylenes present in the reaction mixture. Since some 1,2- butadiene and 1-butyne may be swept through the system with the other components of the gaseous mixture without reacting with lithium, excess 1,2-butadiene and 1-butyne over the theoretical 2:3 molar ratio is normally provided to the reaction system. The principal reactions which occur may be depicted as:

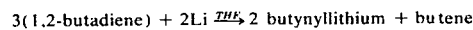

3(1,2-butadiene) + 2Li $\xrightarrow{THF}$ 2 butynyllithium + butene

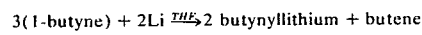

3(1-butyne) + 2Li $\xrightarrow{THF}$ 2 butynyllithium + butene

In carrying out the present process, the lithium reactant is preferably incorporated into the strong coordinating ether solvent and the gaseous 1,2-butadiene or mixture of 1,2-butadiene, 1,3-butadiene, 1-butyne and 2-butyne is then added until the reaction is essentially complete as can be determined visually by noting the disappearance of the lithium particles and their replacement by white or off-white particles of butynyllithium. While not necessary, it has been found that the reaction between the lithium metal and the gaseous hydrocarbon will proceed more quickly and smoothly if small quantities, e.g. about 1 to about 15 mol%, of an alcohol or primary or secondary amine or diamine are added to the slurry or dispersion of lithium metal prior to addition of the gaseous hydrocarbon.

In accordance with the preferred practice, the reaction mixture is agitated well during the addition of the gaseous hydrocarbon and while agitation can be accomplished simply by bubbling the gaseous hydrocarbon into the reaction mixture and also by refluxing, it is preferred to provide additional agitation, as by stirring vigorously. The gaseous hydrocarbon may also be dissolved in a portion of the strong coordinating ether solvent such as tetrahydrofuran and the solution added to the slurry or dispersion of lithium metal.

The slurry of lithium metal and gaseous hydrocarbon is advantageously heated during the reaction, generally from about 30°C. to about 65°C., preferably from about 50°C. to about 60°C., thereby insuring a maximum rate of reaction. In addition, the reaction is preferably carried out in a substantially oxygen-free atmosphere, as under a blanket of an inert gas such as argon, helium and the like.

On completion of the reaction, the butynyllithium product may be utilized as a slurry or recovered as a solid product through filtration and washing with a diethyl ether or pentane. The butynyllithium obtained is relatively pure and is recovered in high yield.

When a gaseous mixture of 1,2-butadiene, 1,3-butadiene, 1-butyne and 2-butyne is utilized in the foregoing method, the 2-butyne component remains substantially inert, participating slightly, if at all, in the reaction. This, of course, lowers the yield of butynyllithium. In preferred embodiments of this invention, it has been found that the yield of butynyllithium can be increased by forming an adduct of the lithium reactant and a polycyclic aromatic hydrocarbon prior to the addition of the 2-butyne containing gaseous hydrocarbon mixture. The adduct is formed through the addition of 5 to 100 mol percent of the polycyclic aromatic hydrocarbon such as naphthalene, substituted naphthalanes or diphenyl to the dispersion or slurry of lithium metal in the strong coordinating ether solvent. In this manner, the 2-butyne component of the gaseous hydrocarbon undergoes more complete reaction thereby increasing the yield of butynyllithium.

In another preferred embodiment, it also has been found that the yield of butynyllithium can be increased through the addition of 0.5 to 6 mol percent of ammonia to the dispersion or slurry of lithium metal in the strong coordinating ether solvent prior to addition of the gaseous hydrocarbon reactant. Sufficient ammonia is added to form a copper-gold colored lithium-ammonia complex which combines rapidly with 1,2-butadiene or a mixture of 1,2-butadiene, 1,3-butadiene, 1-butyne and 2-butyne.

Butynyllithium is a compound of general utility in the synthesis of various fragrances and pharmaceutical compounds.

The following illustrative examples are provided to facilitate an understanding of the present invention.

EXAMPLE 1

A round bottom, three-necked flask equipped with a stirrer, gas inlet tube, thermometer, reflux condenser and a heating mantle is flushed with argon. The flask is then charged with 4.9 g. pure lithium metal powder and 250 ml. of tetrahydrofuran. The slurry is heated to 55°C. and 20 g. of a gaseous mixture containing about 28% 1,2-butadiene, 3% 1-butyne, 28% 2-butyne, and 39% 1,3-butadiene, the balance (about 2%) being isomeric butenes is bubbled therethrough with constant agitation over a period of 1.5 hours. The mixture is stirred under this gas at 55°C. until it achieves a white to off-white color and the lithium metal disappears. The mixture is then cooled to 20°C., filtered and the product residue is washed with diethyl ether. The white butynyllithium powder recovered weighs 33 g. and contains 10.5% lithium for a yield of 92% based on a lithium analysis and calculates 91% purity. Six g. of dimers and trimers of 1,3-butadiene were also isolated in the filtrate.

EXAMPLE 2

Following the procedure of Example 1, 7 g. of lithium metal and 250 ml. of tetrahydrofuran are added to the flask and heated to 50°–55°C. and 350 g. of the gaseous mixture described in Example 1 is bubbled therethrough with constant stirring over a 2 hour period. The mixture is stirred under this gas at 50°–55°C. until it achieves a white to off-white color and the lithium metal disappears. The mixture is then cooled to 20°C., filtered and the product residue is washed with pentane and dried under a vacuum of 1mm. Hg. The white butynyllithium powder recovered weighs 63 g. and contains 11.2% lithium for a yield of 97% based on lithium analysis. 8 g. of dimers and trimers of 1,3-butadiene were isolated in the filtrate.

EXAMPLE 3

Following the procedure of Example 1, 4.8 g. of lithium metal powder and 250 ml. of 1,2-dimethoxymethane are added to the flask and heated to 55°–60°C. with constant stirring over a 2-hour period. The mixture is then cooled to 20°C., filtered and the product residue is washed and dried for 1 hour under a vacuum of 0.2 mm Hg. The white butynyllithium powder recovered weighs 28 g. for a yield of 66% based on lithium analysis. 35 g. of 1,3-butadiene dimers and trimers were isolated from the solution.

EXAMPLE 4

Following the procedure of Example 1, but with a pressure equalizing dropping funnel in place of the gas addition tube, 100 g. of naphthalene (0.77 moles) were added to 7.3 g. of lithium metal powder (1.05 moles) in 100 ml. tetrahydrofuran forming a dark green-brown lithium-naphthalene adduct over a period of about 30 minutes. 168 g. of the gaseous hydrocarbon mixture of Example 1 dissolved in 800 ml. tetrahydrofuran were added to the flask over a two hour period while maintaining the slurry at a temperature of about 55°C. Near the end of the addition, the slurry turned to an olive green color and became light brown after stirring for an additional hour. An aliquot of the resultant product was reacted with 1-hexanal producing 3-decyn-5-ol which, by gas chromotograph analysis, establishes a yield of butynyllithium in excess of 90%, based on lithium.

EXAMPLE 5

Following the procedure of Example 1, but with a pressure equalizing dropping funnel in place of the gas addition tube, 5.2 g. of lithium metal powder and 125 ml. of tetrahydrofuran are added to the flask. 65 g. of ammonia gas is condensed into the slurry with stirring forming a liquid-copper-gold colored lithium ammonia adduct. 190 g. of a mixture containing about 18% 1,2-butadiene, 21% 1,3-butadiene, 4% 1-butyne, 3.3% 2-butyne and about 25% isomeric butenes dissolved in 800 ml. tetrahydrofuran was added over a 70 minute period with stirring while maintaining the temperature at about 50°C. to 60°C. The mixture was refluxed to drive off excess gases and cooled. An aliquot of the product was reacted with 1-hexanal producing 3-decyn-5-ol which by gas chromotograph analysis, establishes a yield of butynyllithium in excess of 90%, based on lithium.

EXAMPLE 6

When an attempt is made to follow the procedure of Example 1 using lithium metal containing 1% sodium the yield of butynyllithium is reduced and a polymeric oil is formed.

EXAMPLE 7

When an attempt is made to follow the procedure of Example 1 using sodium metal in place of lithium metal extensive polymerization occurs and a gel forms.

EXAMPLE 8

When an attempt is made to follow the procedure of Example 1 using lithium metal in xylene, benzene and diethyl ether with the gaseous mixture, little or no reaction is observed.

Having thus described the invention, what is claimed is:

1. A process for preparing butynyllithium which comprises passing a gaseous unsaturated hydrocarbon selected from the group consisting of 1,2-butadiene or a mixture of 1,2-butadiene, 1,3-butadiene, 1-butyne and 2-butyne, said mixture containing from about 5% to about 100%, by weight, of 1,2-butadiene, 1,3-butadiene, 1-butyne and 2-butyne components, into a slurry of finely-divided lithium metal dispersed in a strong coordinating ether solvent, said slurry being under a substantially oxygen-free atmosphere, said hydrocarbon and said lithium metal being combined in a mol ratio of about 2:3.

2. The process of claim 1 wherein the strong coordinating ether solvent is selected from the group consisting of tetrahydrofuran, tetrahydropyran, dioxane, ethylene glycol dimethyl ether, ethylene glycol diethyl ether the dimethyl and diethyl ethers of diethylene, triethylene and tetraethylene glycols and mixtures of two or more of said solvents.

3. The process of claim 2 wherein the solvent is tetrahydrofuran.

4. The process of claim 1 wherein the process is carried out at a temperature of from about 30°C. to about 65°C.

5. The process of claim 1 wherein from about 5 to about 100 mol percent of a polycyclic aromatic hydrocarbon selected from the group of naphthalene, substituted naphthalenes and diphenyl is combined with said lithium metal prior to addition of said gaseous unsaturated hydrocarbon.

6. The process of claim 1 wherein ammonia is combined with said lithium metal prior to addition of said gaseous unsaturated hydrocarbon.

7. The process of claim 1 wherein said hydrocarbon mixture contains not more than 60%, by weight, 1,3-butadiene.

8. The process of claim 1 wherein said hydrocarbon mixture contains from about 15% to about 100%, by weight, of 1,2-butadiene, 1,3-butadiene, 1-butyne and 2-butyne components.

* * * * *